US00PP07887P

United States Patent [19]

van Andel

[11] Patent Number: Plant 7,887

[45] Date of Patent: Jun. 16, 1992

[54] FREESIA VARIETY NAMED VARARED

[75] Inventor: Jacob van Andel, Aalsmeer, Netherlands

[73] Assignee: Van Staaveren B.V., Aalsmeer, Netherlands

[21] Appl. No.: 560,099

[22] Filed: Jul. 30, 1990

[51] Int. Cl.[5] ..... A01H 5/00

[52] U.S. Cl. ..... Plt./68

[58] Field of Search ..... Plt./68

*Primary Examiner*—James R. Feyrer

[57] ABSTRACT

A new and distinct Freesia cultivar distinguished by its very tall stems bearing a single red flower at its upper end and immediately preceeding a jointed rachis which extends almost at right angles to the stem and has from six to nine longitudinally spaced buds of which several may be open at the same time, the flowers being of medium size and blooming successively on strong spikes with substantially uniform spacing along the rachis to its end.

1 Drawing Sheet

BACKGROUND OF THE NEW PLANT

My new Freesia cultivar originated as a seedling of a hybrid produced by my crossing two varieties selected from a collection of Freesias being maintained at my nursery at Aalsmeer, Holland for breeding purposes with the object of producing Freesia hybrids that can be grown faster and at higher temperatures than ordinary Freesia hybrids. This particular seedling was selected because of its medium red flowers and numerous buds, the height of the main stem and its apparent growth habits that meet my breeding objectives.

This new Freesia is not being produced and grown at Aalsmeer from selected cormes and cormels of the parent plant and its clones with very satisfactory results.

DESCRIPTION OF THE DRAWING

My new Freesia cultivar is illustrated by the accompanying full color photographic drawing which shows several stems illustrating the nature of the buds and the first production of flowers, the color rendition being as nearly true to that herein specified as is reasonably possible to obtain by professional photographic procedures.

DESCRIPTION OF THE NEW PLANT

The following is a detailed description of my new Freesia cultivar as observed from plants grown at Aalsmeer, Holland, with color designations being according to The R.H.S. Colour Chart published by The Royal Horticultural Society of London, England.

THE PLANT

Origin: Seedling.

Parentage:

*Hybrid seed parent.*—Variety No. 7130 AS2.

*Pollen parent.*—Variety No. 6135 DS2. Both varieties being grown at Aalsmeer and noted in breeding records continuously maintained in nursery office at Aalsmeer.

Classification:

*Botanic.*—Freesia hybrid.

*Commercial.*—Freesia.

Form: A sturdy, upright and vigorous stem.

Height: Up to about 100 cm.

Stem length: About 100 cm.

Branching character: None.

Foliage:

*Quantity.*—5 to 12 leaves depending on growing temperature.

*Shape.*—Oblong with entire margins.

*Texture.*—Smooth.

*Color.*—Middle green.

Corms:

*Color.*—White with brown scales.

*Size.*—Varying with age with circumference of 30 to 90 mm.

THE BUD

Shape: Long, ovate with obtuse tip.

Diameter: About 15 mm.

Length: About 55 mm.

Rate of opening: Medium.

Color:

*When petals begin to unfurl.*—RHS 34-A.

*When flowers open, both inside and outside.*—RHS 34-A/44-A.

Calyx:

*Shape.*—Tubular.

*Size.*—Small.

*Aspect.*—Smooth.

INFLORESCENCE

Blooming habit: Intermittent; once early.

Size of bloom:

*Diameter.*—About 45 mm.

*Depth.*—About 70 mm.

Shape:

*When bloom first opens.*—Cup shaped.

*When bloom matures.*—The opening widens somewhat.

Petalage:

*Number.*—6.

*Arrangement.*—Tubular-Imbricated.

*Texture.*—Soft.

*Appearance.*—Velvety.

*Color.*—Body — 34-A/44-A, the darker red 44-A being at the petal margins and tips. Inner portion or base — Indian Yellow, 17-B.

Discoloration after full bloom: Reddish/Brown.

Persistence: The flowers hang on and dry.

Fragrance: Very fragrant.

Disease resistance: Resistan to fusarium, oxysporum as observed at Aalsmeer, Holland.

Lasting quality:

*On plant.*—18 days.

*As cut flower.*—7 days.

I claim:

1. The new and distinctive Freesia cultivar, substantially as herein shown and described, and distinguished by the height of its sturdy upright stem, its many buds and medium red flowers.

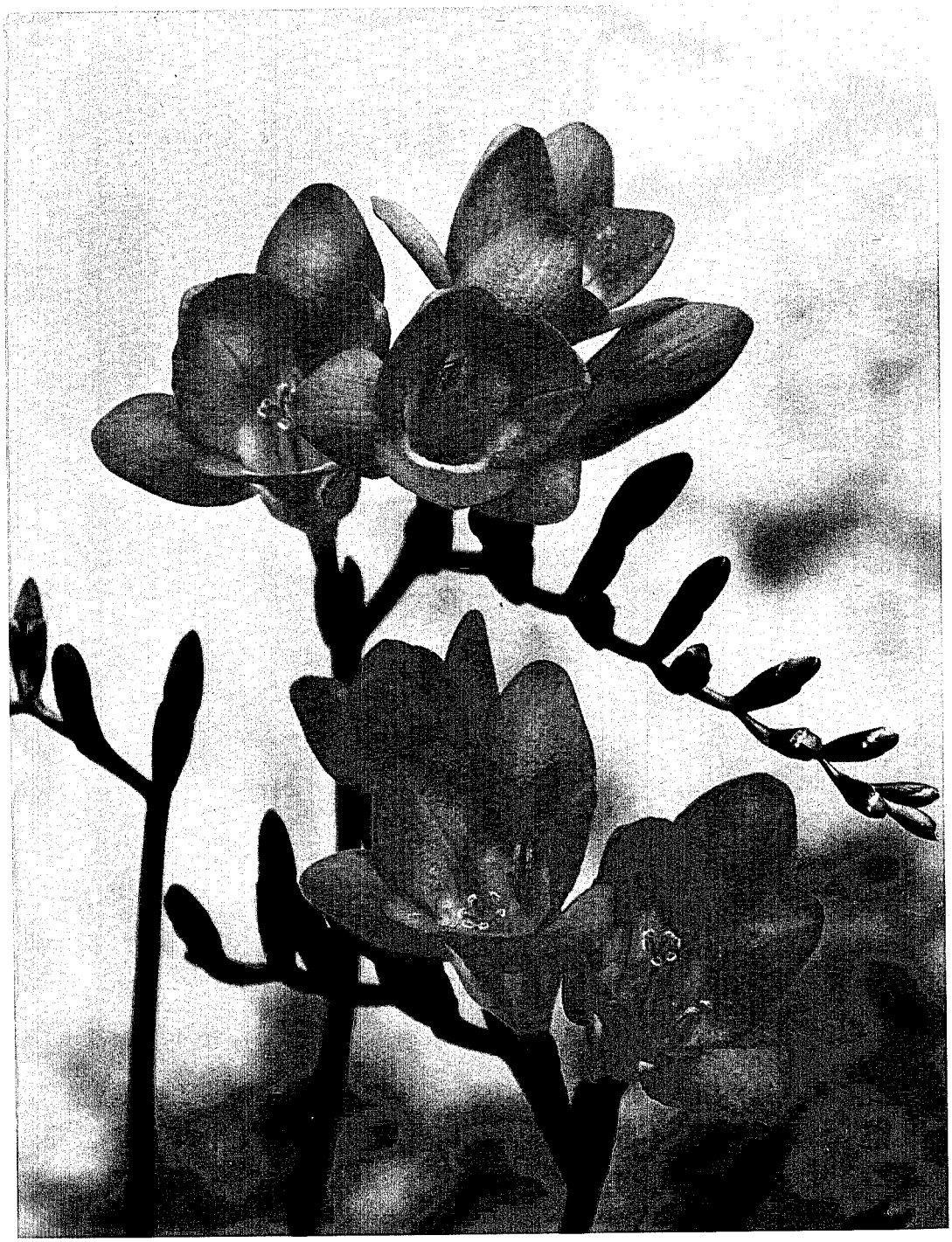

* * * * *